(12) United States Patent
Sherer

(10) Patent No.: US 7,552,390 B1
(45) Date of Patent: Jun. 23, 2009

(54) RECORDATION AND ORGANIZATION OF PROBLEM SOLVING DATA

(75) Inventor: F. Alexei Sherer, Escondido, CA (US)

(73) Assignee: Family Vet, Inc., Escondido, CA (US)

( * ) Notice: Subject to any disclaimer, the term of this patent is extended or adjusted under 35 U.S.C. 154(b) by 429 days.

(21) Appl. No.: 11/280,693

(22) Filed: Nov. 16, 2005

Related U.S. Application Data

(62) Division of application No. 10/188,406, filed on Jun. 28, 2002, now Pat. No. 7,254,782.

(60) Provisional application No. 60/302,120, filed on Jun. 29, 2001.

(51) Int. Cl.
*G06F 3/00* (2006.01)

(52) U.S. Cl. .................. 715/744; 715/764; 715/781; 715/809

(58) Field of Classification Search .......... 715/744, 715/764, 781, 809
See application file for complete search history.

(56) References Cited

U.S. PATENT DOCUMENTS

| | | | |
|---|---|---|---|
| 4,404,639 A | 9/1983 | McGuire et al. | |
| 5,745,096 A * | 4/1998 | Ludolph et al. | 715/764 |
| 5,873,095 A * | 2/1999 | Gore | 707/200 |
| 5,874,958 A * | 2/1999 | Ludolph | 715/781 |
| 6,047,259 A | 4/2000 | Campbell et al. | |
| 6,651,216 B1 | 11/2003 | Sullivan et al. | |
| 6,791,581 B2 * | 9/2004 | Novak et al. | 715/744 |
| 7,000,181 B2 * | 2/2006 | Press | 715/212 |

2003/0098891 A1  5/2003  Molander

OTHER PUBLICATIONS

Williams et al. Patient safety—incorporating drawing software into root cause analysis software. J Am Med Inform Assoc. 2000;9(Nov.-Dec. suppl):S52-S53.

(Continued)

*Primary Examiner*—Tadesse Hailu
*Assistant Examiner*—Michael Roswell
(74) *Attorney, Agent, or Firm*—Knobbe Martens Olson & Bear LLP

(57) ABSTRACT

A data model uses a graphical user interface (GUI) for recording and organizing information regarding an object of care. The GUI enables a user to input an observation data set including a plurality of observations, the plurality of observations include at least a first subset of the plurality of observations and a second subset of the plurality of observations. The GUI enables the user to input an action data set including a plurality of actions, the plurality of actions includes at least a first subset of the plurality of actions and a second subset of the plurality of actions. The GUI enables the user to connect a first category of care to at least the first subset of the plurality of observations and at least the first subset of the plurality of actions, and to connect a second category of care to at least the second subset of the plurality of observations and at least the second subset of the plurality of actions, such that each connection indicates a relationship between the respective connected data.

5 Claims, 13 Drawing Sheets

OTHER PUBLICATIONS

Johnson, S., PhD, Generic data modeling for clinical repositories. JAMIA 1996;3:328-339.

Poon et al. The PEN-Ivory project: exploring user-interface design for the selection of items from large controlled vocabularies of medicine. JAMIA 1996;3:168-183.

Thews et al. A graph-grammar approach to represent causal, temporal and other contexts in an oncological patient record. Meth Inform Med 1996;35:127-41.

Hayes, G. The requirements of an electronic medical record to suit all clinical disciplines. 1997 Yearbook of Medical Informatics; pp. 75-82.

Teitelbaum et al. The effects of positional constancy on searching menus for information. CHI'83 Proceedings 1983.

Kushniruk et al. Assessment of a computerized patient record system: a cognitive approach to evaluating medical technology. M.D. Computing 1996; 13(5):406-415.

Smith et al. Data model development as a prelude to implementing a hospital information system. © ISA 1997—Paper #97-044; pp. 263-268.

Tange et al. The granularity of medical narratives and its effect on the speed and completeness of information retrieval. Journal of the American Medical Informatics Association 1998;5(6):571-582.

Nadkarni et al. Managing attribute—value clinical trials data using the ACT/DB client-server database system. Journal of the American Medical Informatics Association 1998;5(2):139-151.

Nadkarni et al. Data extraction and Ad Hoc query of an entity-attribute-value database. Journal of the American Medical Informatics Association 1998;5(6):511-527.

Nadkarni et al. Organization of heterogeneous scientific data using the EAV/CR representation. Journal of the American Medical Informatics Association 1999;6(6):478-493.

Nadkarni et al. WebEAV: Automatic metadata-driven generation of Web interfaces to entity-attribute-value databases. Journal of the American Medical Informatics Association 2000;7(4):343-356.

Chen et al. Exploring performance issues for a clinical database organized using an entity-attribute-value representation. Journal of the American Medical Informatics Association 2000;7(5):475-487.

Nadkarni, QAV: Querying Entity-Attribute Value Metadata in a Biomedical Database, Computer Methods and Programs in Biomedicine (1997) 53:93-103.

Lawrence L. Weed, M.D., "Medical Records that Guide and Teach", *M.D. Computing*, vol. 10, No. 2, 1993.

P. Salmon, M.A. Bainbridge and G. Hayes, "Episode handling in GP records", *Healtcare computing 1997*, pp. 294-300.

* cited by examiner

RECORDATION AND ORGANIZATION OF PROBLEM SOLVING DATA

RELATED APPLICATIONS

This application is a divisional of U.S. application Ser. No. 10/188,406 filed Jun. 28, 2002 now U.S. Pat. No. 7,254,782 which claims priority to U.S. Provisional Patent Application No. 60/302,120 filed on Jun. 29, 2001, which are hereby incorporated by reference in their entirety.

BACKGROUND OF THE INVENTION

1. Field of the Invention

The invention relates to storage of information, and more specifically to a system and method of linking observation data, categories of care data, and action data.

2. Description of the Related Technology

In most service industry occupations, there is a need for record keeping in order to track the progress of the object of care. For example, doctors keep records concerning each of their patients, mechanics keep records of each serviced vehicle, a school administration office may keep discipline records for each student, and a technical support department may keep records of each of their callers. These records are generally taken in an attempt to allow future readers to quickly ascertain the past history of the specific object of care (object of care and object, as used herein, refer generically to the person or item receiving the service, such as a patient, client, customer, automobile, student, etc.). In addition, many records attempt to show a connection between observations made regarding the object, a diagnosis of each condition, and a history of actions taken in an attempt to remedy each condition.

Record keeping has been accomplished in the past using a variety of different methods. For example, a doctor may use a blank piece of paper to write down his patient observations, diagnosis, and treatments given. This record may then be filed in a patient file until the next patient visit. When the patient next visits the doctor, there is no orderly method of locating observations, diagnosis, and actions taken by the doctor on prior visits. The doctor typically must skim the prior record to find the needed information. In addition, it may be difficult, if not impossible, to determine which observations led to each diagnosis, and what actions were taken for each diagnosis. Furthermore, if the doctor wants to add additional observations that relate to a diagnosis given on a prior visit, there is no physical space on the paper and no method of easily indicating that the new observations are directly related to the prior diagnosis. This problem becomes more apparent when a patient has multiple diagnoses. Similarly, if the doctor wishes to record additional treatments given for a prior diagnosis, they are likely listed on the next available blank line on the paper, which may not be adjacent to the prior diagnosis for which the treatments are prescribed. This may make it difficult to quickly determine what observations and diagnosis led to the newly listed treatments. In other words, the reader must decipher which findings led the writer to believe specific problems existed and for which specific problems which actions were taken. Thus, a record from which a reader may easily ascertain 1) why the doctor thought specific problems existed and 2) what the doctor prescribed for each problem, is desirable. It may be very time consuming to determine the answers to these questions with current medical records In another existing method, the doctor may divide findings, or observations, regarding the patient into Subjective (reported by the patient) and Objective (observed by the doctor on exam) observations. The doctor may then record in a different section an assessment of why particular findings caused the doctor to think that there is a particular problem, what the probability of that problem is and the diagnosis. From there, the doctor may record plans, or actions, to hopefully remedy patients problems. This method of recording data is commonly known as the S O A P method. The SOAP model was first introduced in the article titled, "Medical records that Guide and Teach" by Lawrence L. Weed, M. D. (N Engl. J. Med 1968; 278: 593-600) and relates generally to the problem oriented medical record. More specifically, SOAP refers to the process of recording subjective and objective observations, diagnosed problems or situations, and scheduled actions or treatments. Using the SOAP model, the doctor is ideally supposed to write a SOAP note for each perceived problem in the patient. In many cases, some findings are used in the SOAP note for more than one problem and even more frequently plans may be performed for more than one problem. Thus, the SOAP model inherently involves repeated double entry of observations, diagnoses, and actions. A system that prevents double entry of information is desirable.

Previous methods may use paper medical record forms that have boxes for entry of various types of data. Unfortunately, it is difficult for a service provider to determine how much of a particular type of data will need to be recorded, and, thus, the box may constrain the space leading to either incomplete data collection or notes scribbled in margins nearby or elsewhere on the form in another box.

In one prior medical record embodiment, the medical records are source oriented with data stored according to its source. For example, lab results may be kept together, the doctors notes may be kept together and x-ray reports may be kept together. They may all be kept in one chart, but creating a mental model of the patient at any given point in time requires paging through the records from a specific point in time in each of the source groupings.

SUMMARY OF CERTAIN INVENTIVE ASPECTS

The invention relates to a system and method of recording and organizing data corresponding to an object of care. More specifically, the invention relates to a recording system, that may be implemented on a computer system, that organizes data corresponding to an object of care, such that each observation and action is connected to either a specific category of care or multiple categories of care. Throughout the application, a software implementation of the invention, titled 'Soap-Cycle' will be described. However, the invention includes other embodiments than those described below.

In one embodiment, the present invention relates to a data model for recording and organizing information regarding an object of care in a database, the data model comprising an observation data set including a plurality of observations regarding the object of care, a category of care data set including a plurality of categories of care regarding the object of care, an action data set including a plurality of actions regarding the object of care, and a plurality of associations (which may be graphically represented by connection lines), associating each of the plurality of categories of care to one or more of the plurality of actions and to one or more of the plurality of observations.

In another embodiment, the present invention relates to a method of displaying a medium readable by a computing system for executing a computer process for recording and connecting data objects relating to an object of care so that the data objects are connected in a manner that allows a user to determine a logical relationship between a plurality of data objects by viewing the connections between the plurality of data objects. The method comprises receiving a plurality of observations regarding the object of care from a user controlled input device, receiving a plurality of categories of care regarding the object of care from the user controlled input device, receiving a plurality of actions regarding the object of care from the user controlled input device, receiving a plurality of entries from the user controlled input device indicating one or more specific observations that are to be connected to each specific category of care, receiving a plurality of entries from the user controlled input device indicating one or more specific actions that are to be connected to each specific category of care; storing data corresponding to the specific observations and the specific actions that are to be connected to each specific category of care, and sending a GUI to an output device, the GUI including the plurality of observations, the plurality of categories of care, the plurality of actions, and a plurality of connections corresponding to the stored data, wherein the connections are visible as solid lines.

In another embodiment, the invention relates to a data model for recording and organizing information regarding an object of care comprising an observation data set including a plurality of observations, the plurality of observations comprising a first subset of the plurality of observations and a second subset of the plurality of observations, an action data set including a plurality of actions, the plurality of actions comprising a first subset of the plurality of actions and a second subset of the plurality of actions, a first category of care connected to the first subset of the plurality of observations and connected to the first subset of the plurality of actions, and a second category of care connected to the second subset of the plurality of observations and connected to the second subset of the plurality of actions, wherein each connection indicates a relationships between the respective connected data. In other embodiments, additional subsets of the plurality of observations are included and the multiple subsets of the plurality of observations can be connected to a single category of care. In other embodiments, additional subsets of the plurality of actions are included and the multiple subsets of the plurality of actions can be connected to a single category of care.

In another embodiment, the invention relates to a data model for recording and organizing information regarding an object of care comprising an observation data set including a plurality N observations, the plurality of observations comprising a first subset of the plurality of observations, wherein the first subset includes a quantity from 1 to N of the plurality N observations, and a second subset of the plurality of observations, wherein the second subset includes a quantity from 1 to N of the plurality N observation. The data model further includes an action data set including a plurality M of actions, the plurality M of actions comprising a first subset of the plurality M of actions, wherein the first subset includes a quantity from 1 to M of the plurality M actions, and a second subset of the plurality M of actions, wherein the first subset includes a quantity from 1 to M of the plurality M actions. The data model further comprises a first category of care connected to the first subset of the plurality N of observations and connected to the first subset of the plurality M of actions, and a second category of care connected to the second subset of the plurality N of observations and connected to the second subset of the plurality M of actions, wherein each connection indicates a relationship between the respective connected data. In other embodiments, additional subsets of the plurality of observations are included and the multiple subsets of the plurality of observations can be connected to a single category of care. In other embodiments, additional subsets of the plurality of actions are included and the multiple subsets of the plurality of actions can be connected to a single category of care.

In another embodiment, the invention relates to a system for allowing data to be entered into a divider bar, the system comprising a GUI window including a divider bar dividing the GUI window into two separate portions and coupled to a database operable to store a plurality of data, the divider bar having a collapsed state which allows a larger area for display of data above or below the divider bar, and an expanded state configured to allow a user to add new data to the plurality of data, wherein the physical size of the expanded state is larger than the physical size of the collapsed state. The divider bar includes a first selectable button configured to expand the divider bar to the expanded state when the first selectable button is selected, and a second selectable button configured to collapse the divider bar to the collapsed state when the second selectable button is selected. Alternatively, the divider bar includes only one button alternatively labeled either "Expand" or "Collapse" when the bar is collapsed or expanded, respectively. As such, the user may change the state of the divider bar with the same button.

In another embodiment, the invention relates to a method for providing access to a plurality of graphic objects on a computer display. The method comprises (a) creating a generally rectangularly shaped graphic window comprising a plurality of graphic objects organized in an array, (b) creating a generally rectangularly shaped divider graphic object ("divider") operable to separate the graphic window into two portions such that one or more of the plurality of graphic objects are disposed on either side of the divider, the divider comprising a collapsed state and an expanded state, (c) enabling a user to increase the physical area of the divider, when the divider is in the collapsed state, by changing the divider to the expanded state; wherein, in the expanded state the divider contains one or more of the plurality of graphic objects and is operable to accept data input from a user controlled input device, and (d) enabling a user to decrease the physical area of the divider, when the divider is in the expanded state, by changing the divider to the collapsed state; wherein, in the collapsed state the divider is not operable to accept data input from the user controlled input device.

In another embodiment, the invention relates to a system for connecting data objects in a GUI, comprising a plurality of text phrases divided by a plurality of text dividers, wherein each of the plurality of text phrases may be individually selected by a user, wherein when any portion of a particular text phrase is selected, the entire particular text phrase is selected, and at least one connection object, wherein any of the plurality of text phrases may be iteratively selected and connected to one or more of the connection objects, wherein each of the plurality of text phrases that are iteratively selected and connected to the connection object are placed in a first text area disposed apart from each of the plurality of text phrases that are not iteratively selected and connected to the same one or more connection objects.

In another embodiment, the invention relates to a software method for connecting specific text objects with a connection object, the software receives a plurality N of text phrases from a user controlled input device, stores the plurality N of text phrases, displays in a GUI the plurality N of text phrases separated by a plurality N−1 text dividers, and iteratively receives a selection of a specific text phrase from the user controlled input device, receives a selection of connection objects from the user controlled input device, and displays a connection between the selected specific text phrase and the selected connection objects.

BRIEF DESCRIPTION OF THE DRAWINGS

These and other objects and features of the invention will become more fully apparent from the following description and appended claims taken in conjunction with the following drawings, where like reference numbers indicate identical or functionally similar elements.

DETAILED DESCRIPTION OF CERTAIN INVENTIVE EMBODIMENTS

Figure 1:
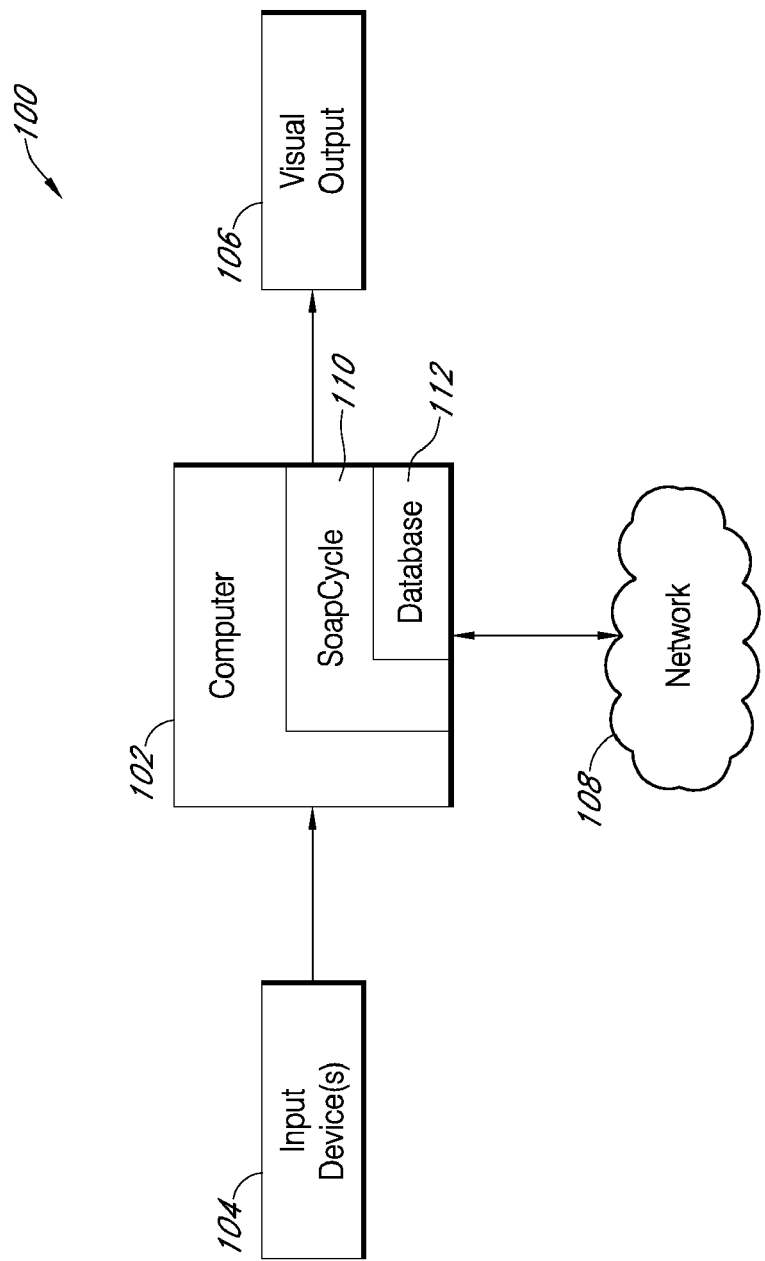
FIG. 1 is a block diagram of a typical computer system on which the software of the invention, SoapCycle, may be executed in one embodiment of the invention.

The following presents a detailed description of certain specific embodiments of the invention. However, the invention can be embodied in a multitude of different ways as defined and covered by the claims. FIG. 1 is a block diagram of a typical computer system on which the software of one embodiment of the invention, SoapCycle, may be executed. A computer or computing device 102 is connected to an input device 104, a visual output 106, and a network 108. The input 104 may include a keyboard, mouse, touchpad, trackball, microphone, or any other computer input device known in the art. Visual output 106 most commonly comprises a computer monitor, but may also be a projector, television, LCD display, or any other visual output device known in the art.

The computer 102 may operate using any type of processor (e.g. Intel, AMD or Motorola), RAM, hard drive, floppy drive, video card, sound card, and other peripheral devices. Computer 102 may use any off-the-shelf or proprietary operating system, including, but not limited to: MAC OS X, UNIX, LINUX, Disk Operating System (DOS), OS/2, PalmOS, VxWorks, Windows 3.X, Windows 95, Windows 98, Windows NT, Windows 2000, Windows XP, and Windows CE. The computer 102 may be a handheld device, a cellular telephone, or other alternative device.

In certain embodiments, network 108 may be of any topology, including, but not limited to: bus, star, or token ring topologies. The network 108 may cover any amount of spatial distance, including, but not limited to a local area networks (LAN), metropolitan area networks (MAN), wide area networks (WAN), or the internet.

The recordation and organization software termed SoapCycle 110 is software that receives, records, organizes, and outputs information relating to objects of care. Objects of care, as discussed above, may be from one of many service industries, including the medical and automotive repair industries. SoapCycle 110 may execute on the computer 102, receive input from input 104 and send output to visual output 106. The database 112 is written to and read from by SoapCycle 110. In other words, SoapCycle 110 builds the database 112 by adding data to the database 112, and SoapCycle 110 may read data from the database 112 that may be organized, formatted, and sent to the visual output 106. FIG. 1 shows the database 112 as residing on the computer 102, however, one skilled in the art will understand that the database 112 can reside on other computers and be configured to be accessed by SoapCycle 110 through methods known in the art. The database 112 may be organized and maintained in any method known in the art.

In one embodiment, SoapCycle software is programmed in Java so that the interface is platform independent. Following is a list of the basic data objects types and a list of properties associated with data object type. Only objects that represent data are listed. Those that represent various user interface widgets are not described.

Object of Care—the Patient, Item or Object Under Care
   Identification number
   Name
   Number of cycles—number of horizontal blocks in record
   Number of categories—number of unique categories in record SoapCycle User—a Simple Implementation of an Authorized User
   Identification number
   Name
   Password Observation—Data Items that Appear in the Observation Column
   Entry identification number
   Object of Care
   Creation Date—Time stamp
   Cycle number User
   Authentication—how was user authenticated, e.g. password
   Connection set—the group of category connections
   Observation attribute—type of observation, e.g. temperature
   Observation value—value of observation, e.g. 98.6 F
   Observations parameters—not used, available for modifiers Category—Data Items that Appear in the Category Column
   Entry identification number
   Object of Care
   Creation Date-Time stamp
   Cycle number User Authentication—how was user authenticated, e.g. password Category number—allows all fields of the category except the number to change while maintaining a connection back to instances of that category number historically. This allows the user to evolve their understanding and description of a particular category in all respects while maintaining a historical thread back through previous descriptions.

Category type—e.g. problem, diagnosis, normal, prevention

Category value—e.g. cough, cancer, no lameness, vaccination

Category comment—e.g. prognosis, thoughts

Action—Data Items that Appear in the Action Column

Entry identification number

Object of Care

Creation Date—Time stamp

Planned Date-Time—when action intended, default immediate

Cycle number

User

Authentication—how was user authenticated, e.g. password

Connection set—the group of category connections

Invoice number—for later use with financial module

Quantity—e.g. number of pills, minutes of surgery

Charge—amount to charge customer for action

Action type—e.g. prescription, surgery

Action value—e.g. aspirin, hysterectomy

Action parameters—not used, available for modifiers

Action status—e.g. recommended, declined, done

Linked ?—action generates linked observations(Boolean)

Note that Observation, Category, and Action share many properties. This is because they share various interfaces. The cycle number and the connection set are required within the data in order to display within SoapCycle.

Actions and Observations have the Connection set property. Each action and each observation keeps a list of the categories to which it is connected. This allows the user interface to group actions or observations together in a box when they share the same set of connections to categories. And it allows the interface to draw lines between these boxes and the categories to which they are connected.

There are some properties created for future use. Observation parameters could be used to supply information to help interpret the observation. An example would be the normal range of a lab result. Action parameters are used for descriptive information about the action that is not about the object of care. An example would be the exposure settings of an x-ray.

The 'Linked ?' Property of Actions is intended for future use as well. Some actions, such as a physical exam or a blood panel may generate new observations in the next cycle. This flag would be a partial solution to providing the user with a list of all observations resulting from a particular action. Another connection set or similar functionality would be required between each action and resulting observations.

In one embodiment, a category of care entry may be identified as one of three types, namely, diagnosis, preventative care, or normal care. The category of care serves as a central axis, to which observations and actions are linked. As such, future observation or actions related to an existing category of care may be linked to the existing category of care, eliminating the need for double entry. For example, a veterinarian may observe a variety of conditions of a particular dog. These observations may come both from the owner telling the veterinarian about the dog's conditions and the veterinarian making observations once the dog is in his sight. These observations may lead to a plurality of categories of care, for example: normal, diarrhea—severe, and pinched nerve. Each of these three categories of care may be linked to a plurality of observations that led the veterinarian to that particular category of care. For example, the observations 'no stiffness' and 'no vomiting' may be linked to a normal category of care while the observations 'owner reports diarrhea 6 times per day' and 'lack of energy' may be linked to the 'diarrhea—severe' category of care. In addition, according to the invention, each of the actions taken is linked directly to the category of care for which it attempts to remedy. In this way, any future reader may easily ascertain the observations that led the veterinarian to a certain category of care, and further, the actions that were taken to remedy the category of care.

The invention also allows users of an already existing object file to add observations and actions which may be linked to already existing categories of care. Continuing with the veterinarian example above, on a future visit by the same dog the veterinarian may observe additional conditions that imply that the dog has a pinched nerve. These observations may be recorded and linked to the pre-existing category of care 'pinched nerve,' such that the veterinarian need not re-enter the pre-existing category of care. Furthermore the veterinarian may record additional actions taken to remedy a pre-existing category of care and link the actions to the pre-existing category of care.

According to the invention, all data related to a patient or object of care is integrated in to one view. For example, the results of the physical exam, x-ray findings, prescriptions, lab results, and financial charges are not separated in to different windows or tabs so that they all may be viewed together, providing more context and therefore richer meaning to the reader.

Figure 2:
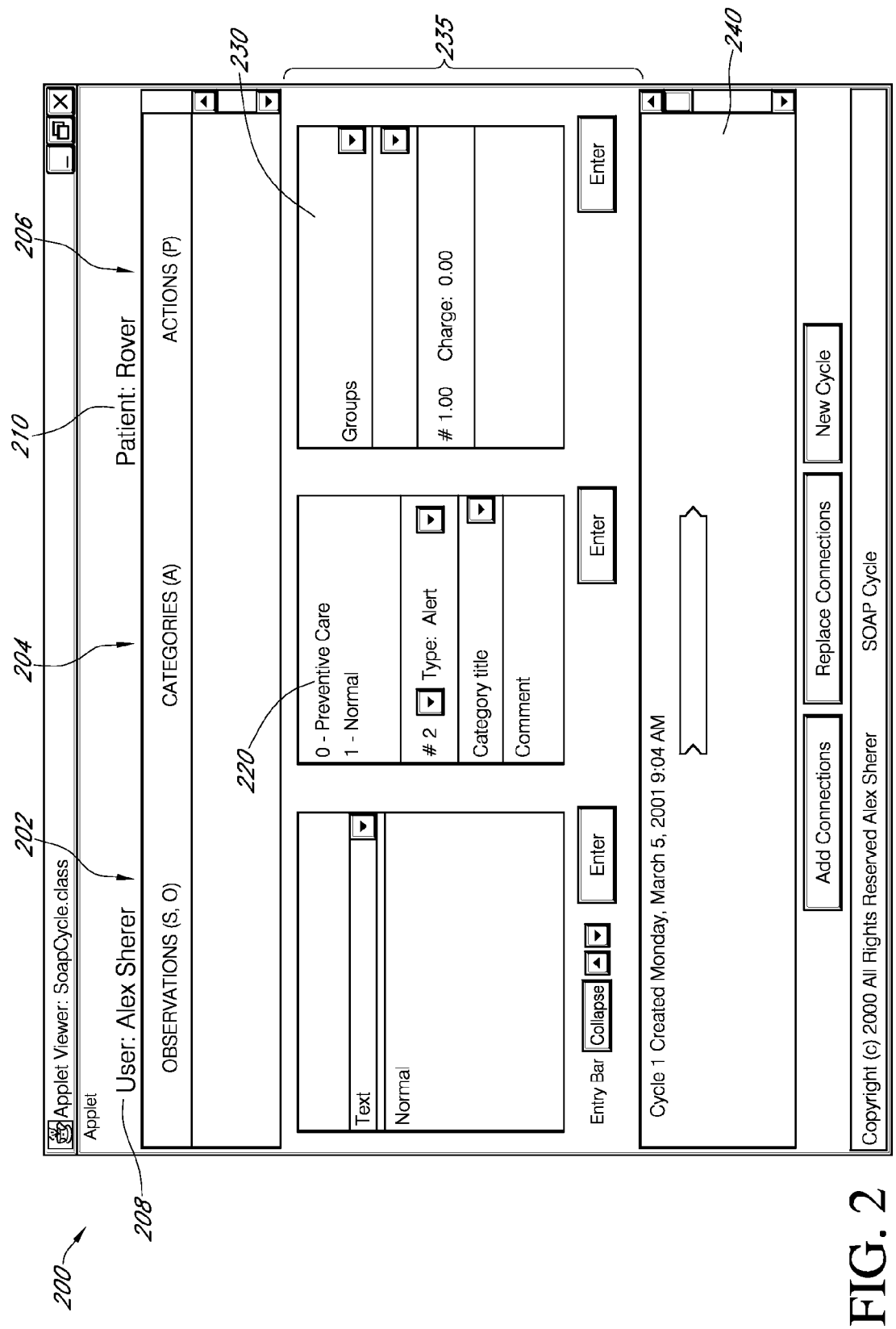
FIG. 2 is a screen shot illustrating the SoapCycle software in the startup state in one embodiment of the invention.
Figure 6:
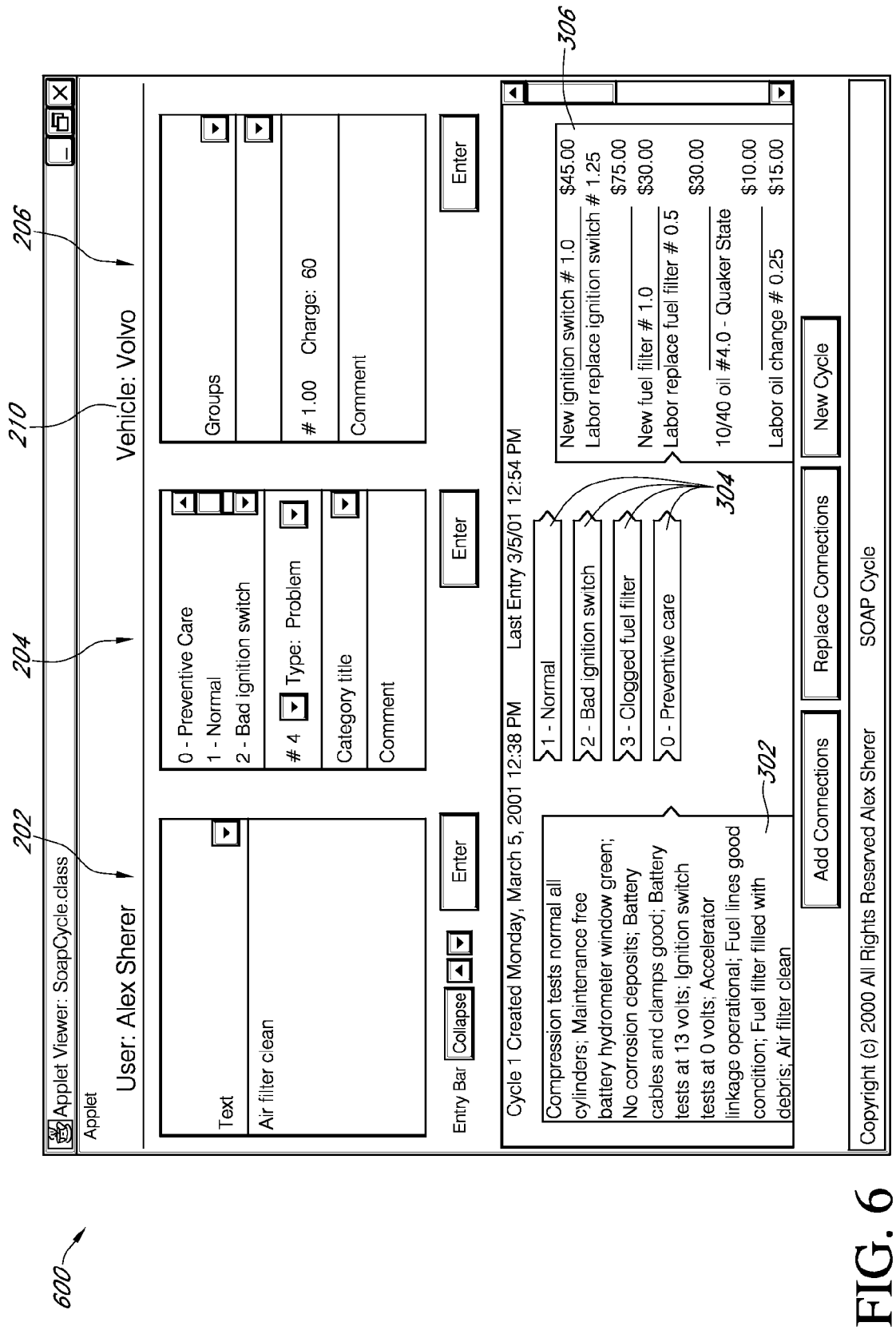
FIG. 6 is a screen shot illustrating the SoapCycle software, used in an automobile repair context, after entering data (observations, categories, and actions), but before adding connections between the three data types in one embodiment of the invention.
Figure 7:
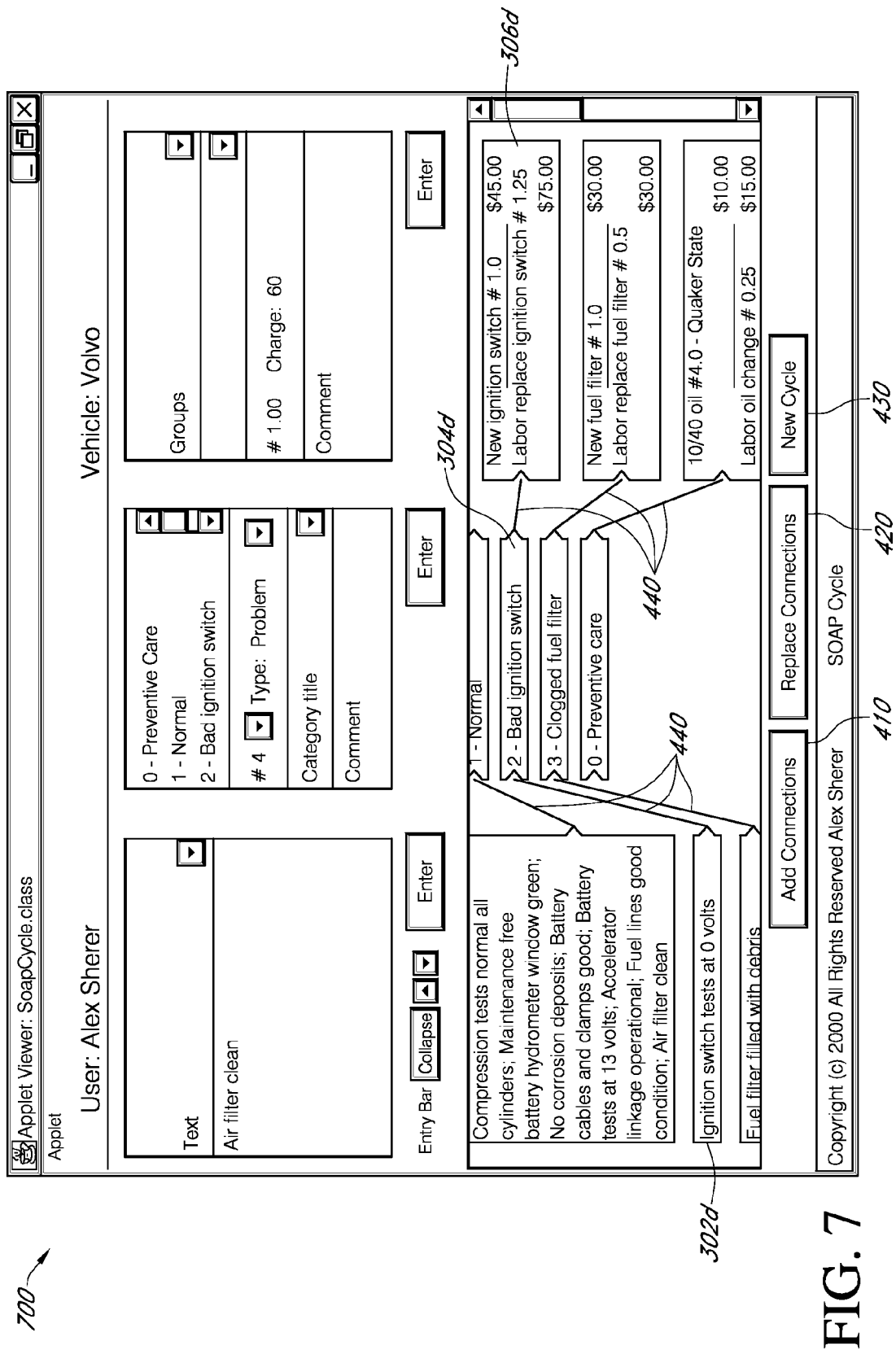
FIG. 7 is a screen shot illustrating the SoapCycle software, used in an automobile repair context, after adding connections between the three data types in one embodiment of the invention.
Figure 8:
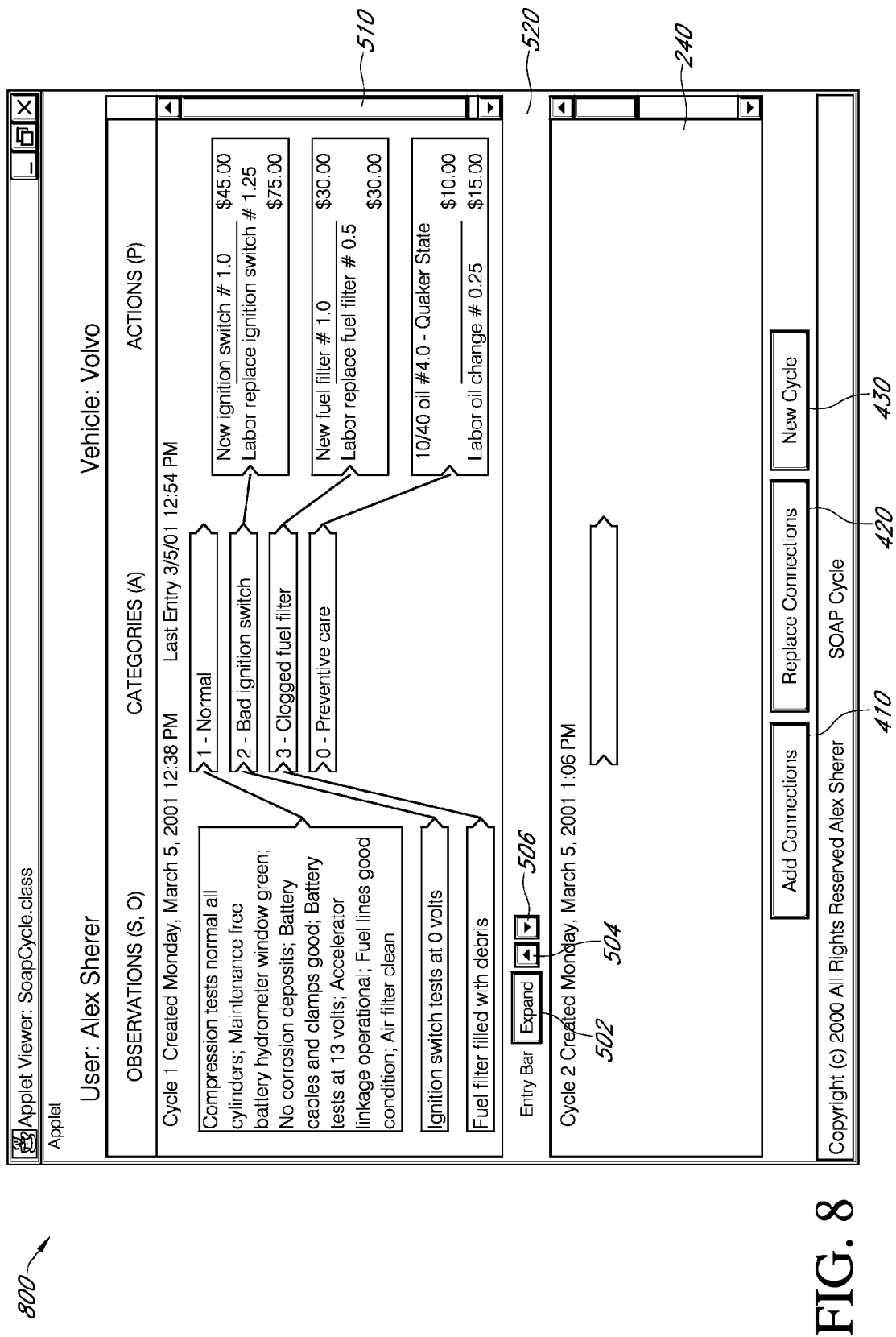
FIG. 8 is a screen shot illustrating the SoapCycle software, used in an automobile repair context, after completing an entry cycle in one embodiment of the invention.

FIG. 2 is a screen shot illustrating one embodiment of the SoapCycle software in the startup state 200. FIGS. 2 through 5 illustrate a version of SoapCycle that has been adapted for use in a medical or veterinarian practice while FIGS. 6 through 8 illustrate a version of SoapCycle that has been adapted for use in an automobile repair company. While these two specific applications of SoapCycle are discussed in detail herein, it is contemplated that the invention may be used by any industry that may keep problem solving records relating to specific objects. For example, the SoapCycle software may be used by a school administration office to keep discipline records for each student, a technical support department may keep records of each of their callers, and a prison may keep records of each inmate. One of ordinary skill in the art may easily adapt the examples explained in the Detailed Description to any other problem solving environment.

The SoapCycle Graphic User Interface ("GUI") is divided generally in to three columns titled observations 202, categories 204, and actions 206. The name of the operator is shown in the user field 208 and the name of the patient is shown in the patient field 210. In one embodiment, the operator must log on, by entering a login name and password, before selecting an existing patient record or creating a new patient record. In another embodiment, the startup state 200 may also show additional patient information, such as species, date of birth, age, sex, breed, coloring, the owners name, and other biographical and billing information corresponding to the owner. These patient information fields may vary depending on the veterinarians preferences and may be easily modified by the veterinarian. Patient information fields may generically be referred to as Object Information Fields which may include, for example, client information fields, customer information fields, or inmate information fields in other service industries. For example, in an embodiment of SoapCycle adapted to computer technical support records, the object information fields may include customer name, address, telephone number, type of computer, and computer knowledge.

The observations column 202 may be used to enter and display observations by the service provider (i.e. the user) regarding the object of care (e.g., an animal in a veterinarian settings or an automobile in a mechanical setting). In the medical field, observations have traditionally been divided into Subjective (S) and Objective (O) observations. Subjective observations refer to information reported by the patient and objective observations refer to information collected by the doctor. In the preferred embodiment, the subjective and objective observations are both recorded in the observations column 202. Because the subjective or objective nature of the data is almost always implicitly obvious (e.g. patient reports coughing for two months verses patient had deep cough during examination), combining all observations in to one column simplifies the record. The categories column 204 may be used to enter and display the categories of care ("categories"), such as normal, diagnosis, or preventative care. The categories are the central organizing axis of the record. After the service provider notes the pertinent observations, an assessment discussing what the observations meant, whether they indicated new problems, or the prognosis may be recorded as a category of care. There may be categories of care that are not necessarily problems, such as preventive or normal care. According to the invention, categories may be added as needed by the specific service provider. Many in the medical field like to distinguish between problems and diagnoses (e.g. cough is a problem, lung cancer is a diagnosis). SoapCycle allows such medical practitioners to create separate categories for problems and diagnoses. Other service industries may also create and use different categories of care.

The actions column 206 may be used to enter and display any actions taken or prescribed, such as x-rays, lab tests, prescriptions, or special instructions. Actions are derived from the plans (P) element of the SOAP model. The actions column 206 may include specific action information that is not specific to the object of care. For example, when taking x-rays, the exposure settings would belong in this column, but any abnormalities found in the x-ray would go in the observations column.

The cycle work area 240 displays all observations, categories, and actions recorded in the current cycle. A cycle is a group of observations, categories and actions.

Figure 3:
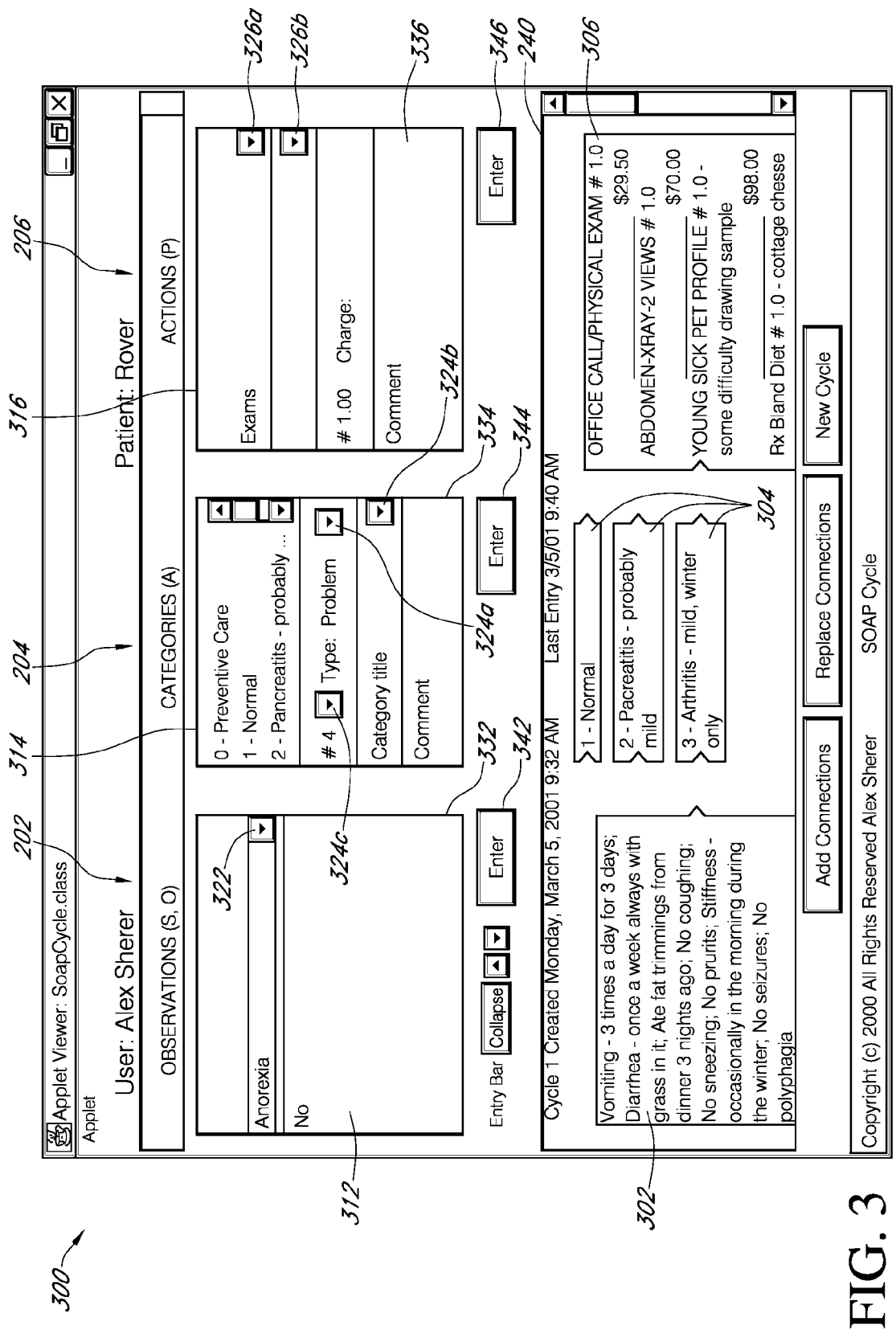
FIG. 3 is a screen shot illustrating the SoapCycle software after entering data (observations, categories, and actions), but before adding connections between the three data types.

FIG. 3 is a screen shot illustrating one embodiment of the SoapCycle software after entering data (observations, categories, and actions), but before adding connections between the three data types. As observations, categories, and actions are added to the patient record, they are listed in the cycle work area 240. For example, an observation is entered in the observation entry block 312 using any combination of pull-down menus and text entry fields. In the embodiment shown in FIG. 3, the observation entry block includes a pull down menu 322 and a text entry field 332. In one embodiment, common observations may be pre-stored in pull-down menu 322 so that the user may quickly select them. The user may also enter other observations, or more details regarding an observation selected in the pull down menu 322, in the text entry field 332. In another embodiment, the operator may add observations to the existing list contained in the pull-down menu 322. It is contemplated that any data entry method known in the art may be used to enter observations in the observation entry block 312. When the user is done entering the observation in the observation entry block 312, the user may click the enter button 342 or push an enter or return key to transfer the current observation to the current cycle work area 240. Each entered observation in a single cycle will initially be placed in a single textlist box 302, separated by semicolons. Thus, each group of text in between semicolons in textlist box 302 is a separately entered observation. For example, in FIG. 3 the user has entered 9 separate observations, namely 'vomiting—3 times a day for 3 days', 'Diarrhea—once a week always with grass in it', 'Ate fat trimmings from dinner 3 nights ago', 'No coughing, 'No sneezing', 'No pruritis', 'Stiffness—occasionally in the morning during the winter', 'No seizures', and 'No polyphagia.' The SoapCycle software may store a time, date, name of user that entered, and authentication method of user that entered (e.g. password authentication) associated with each individual observation, category, and action, which may be visible in a pop-up text box when the pointer is placed over the top of the observation. The 9 separate observations of FIG. 3 are displayed as free text (i.e. not in a list format, but in paragraph format) so that the amount of space required in the GUI may be reduced. For example, if the observations were displayed in a standard list, 9 text lines would be required to display all 9 observations. In addition, although the observations are displayed as free text divided by commas (or any other text divider in other embodiments), each observation may be individually selected (i.e. without selecting an entire row of text) and associated with either a specific category or to multiple categories (discussed below with regard to FIG. 4).

In a similar way as discussed above, categories and actions are entered. Categories may be selected from various pull down menus such as a category type pull down menu 324A, a category title pull down menu 324B and a category number pull down menu 324C. A list of categories in the pull-down menus 324A-C, which allows new categories to be added, and comments may be made in the comment box 334. When a category has been selected or entered, the category may be transferred to the current cycle work area 240 by clicking on the enter button 344 or by pushing a return or enter key. Each category entered will be placed in a separate category box 304. The user may enter actions in a similar fashion, by selecting actions from pull-down menus 326A and 326B and/or entering comments in a comment box 336. The pull down menu 326A is for action groups and the pull down menu 326B is for actions. Making a selection in the menu 326A selects a subset of available actions to be displayed in the menu 326B. Actions may also include a flat billing rate, or, alternatively, a billing time and rate for each individual action. For example, the action of performing a chest x-ray may have a flat billing rate of $70, while the action of performing a surgery may include an hourly billing rate which may be calculated by the SoapCycle software using an entered billing time and rate. When actions are entered (by clicking the actions enter button 346 or by pushing a return or enter key), they are initially placed in a single actions box 306 divided by horizontal lines (or any other dividing means). Like the individual observations, each individual action may be separately selected and linked to at least one category box 304.

Figure 4:
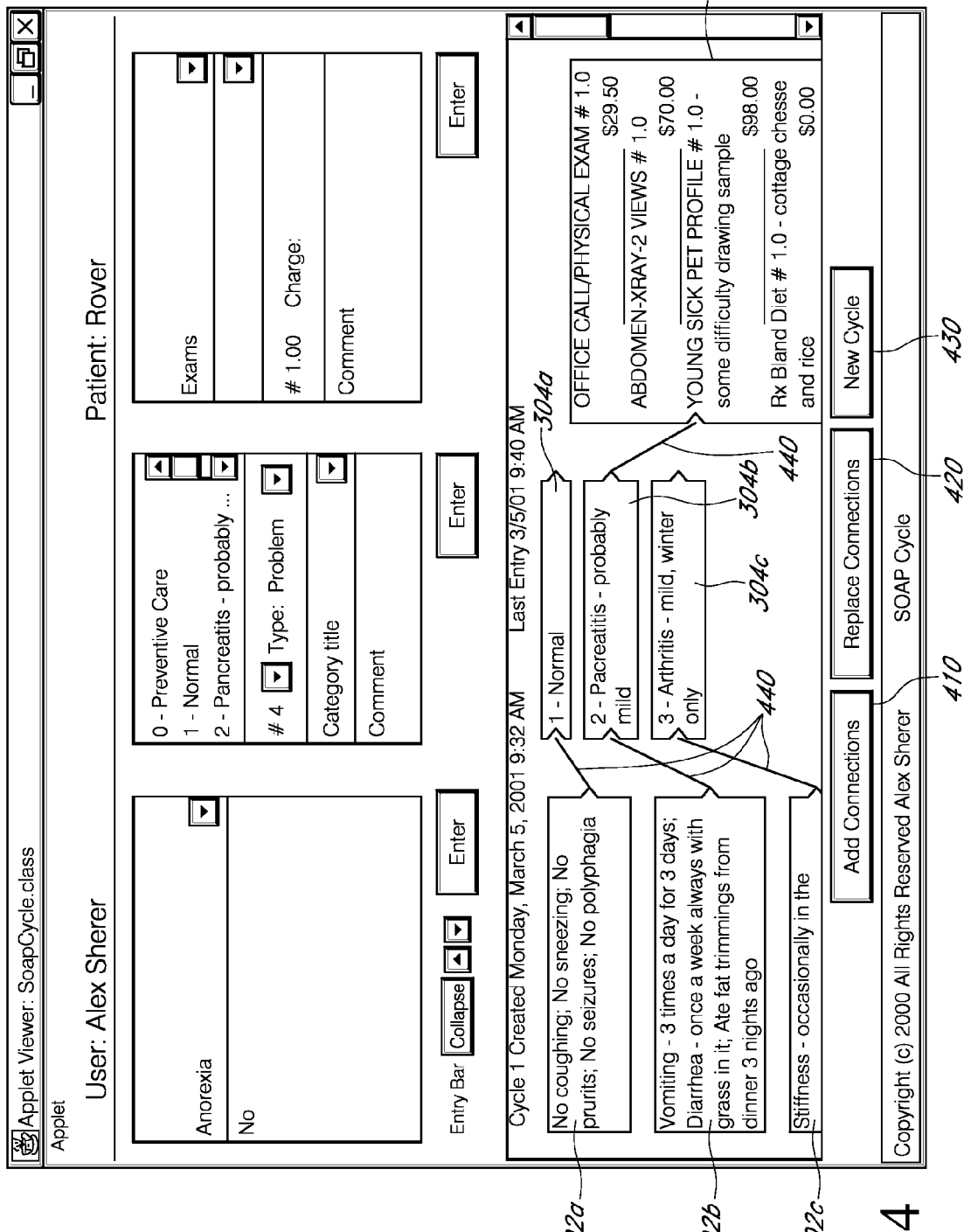
FIG. 4 is a screen shot illustrating the SoapCycle software after adding connections between the three data types in one embodiment of the invention.

FIG. 4 is a screen shot illustrating one embodiment of the SoapCycle software after adding connections between the three data types. Although connections may be created in a variety of different methods, one method will be described hereafter. Each separate observation (i.e. each phrase between semicolons) may be selected by clicking on the phrase. Once a specific phrase is selected the text of that specific phrase may be highlighted. The user may then highlights the category (by clicking on it) which the already selected observation is to be connected to. The connection is made when the Add Connections button 410 is clicked the GUI displays a straight line between the two connected objects. Each remaining observation may likewise be selected and connected to a specific category in the same manner. As each connection is being created the SoapCycle software creates new observation boxes 302 as necessary. In addition, multiple connections may be created simultaneously by selecting multiple observations and one or more categories before clicking the Add connections button 410. For example, the connection between the observation box 302A and the category box 304A may be created by the user clicking on "No coughing", "No sneezing", "No pruritis", "No seizures", and "No polyphagia" in the observations column 202 (FIG. 3), clicking on "Normal" in the categories column 204, and then clicking the Add Connections button 410.

In the embodiment of FIG. 4, individual observation boxes 302 contain observations connected to a specific category. As the user connects multiple observation boxes to a single category box, the multiple observation boxes are consolidated into a single box. FIG. 4 illustrates three observation boxes 302A, 302B, and 302C that have been created as a result of the connections chosen by the user. For example, the three observations 'vomiting—3 times a day for 3 days', 'Diarrhea— once a week always with grass in it', and 'Ate fat trimmings from dinner 3 nights ago' were all connected with the category pancreatitis 304B, and thus all three observations are included in a single observation box 302B, and are connected to the category box 304B with a single connection line. In addition, a specific observation may be connected to multiple categories. If a specific observation is connected to multiple categories, the observation can be listed in an observation box 302 with line connections to the multiple categories. If additional observations share identical connections (i.e. to multiple categories), the observations can share the same observation box 302. Connections between the categories and actions are created in a similar manner. The user clicks on a category, the category is highlighted, the desired action for that category is selected (by clicking on it), and the Add connections 410 button is clicked creating a connection. Each category may have zero, one, or any plurality of actions connected to it. In the example of FIG. 4, the normal category 304A has zero actions connected to it, the pancreatitis category 304B has four actions connected to it, and the arthritis category has zero actions connected to it. Additionally, connections between a specific category, multiple observations, and multiple actions may be created simultaneously by selecting the specific category, along with all observations and actions to be connected to the specific category, and then clicking the Add Connections 410 button.

The Replace Connections button 420 will remove any existing connections attached to the selected observations, category, and actions and create new connections between the selected observations, category, and actions. In other words the Replace Connections button 420 removes connections currently attached to the selected observations or actions and creates new connections between the selected category, observations, and actions.

After all of the connections are made a reader may easily determine the specific observations that led to each specific category of care, and, in addition, what actions were performed or prescribed for each specific category of care.

Figure 5:
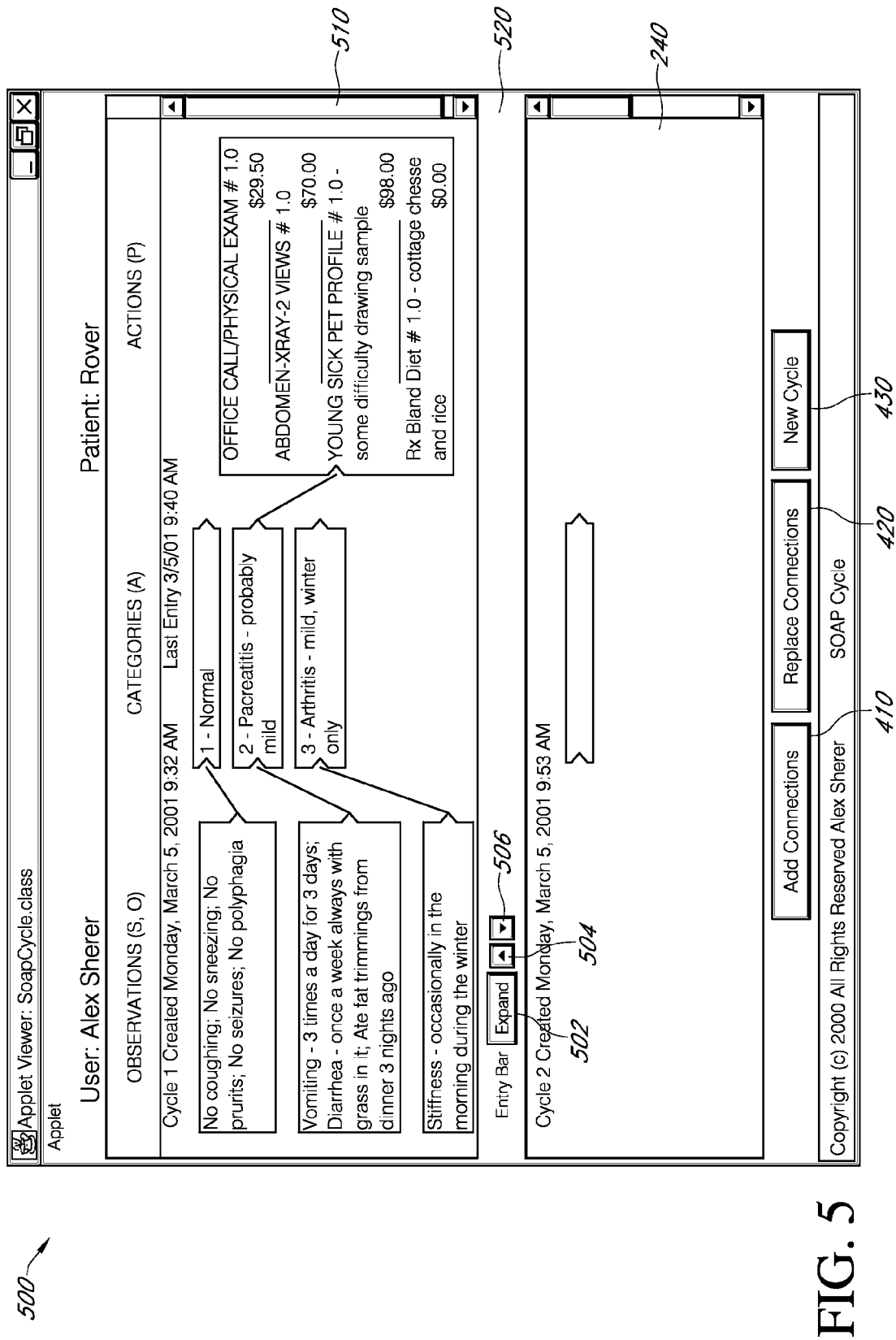
FIG. 5 is a screen shot illustrating the SoapCycle software after completing an entry cycle in one embodiment of the invention.

FIG. 5 is a screen shot illustrating one embodiment of the SoapCycle software after completing an entry cycle. When each observation and action is connected to a category the current cycle is complete. The user may then move the current cycle from the current cycle work area to a cycle history area 510. The entry area 235 (FIG. 2) has been collapsed, hiding the entry area 235, and making visible the cycle history area 510. The cycle history area can be made visible without collapsing the entry area by dragging the divider bar entry area down. In other words, the divider bar motions are available whether the divider bar is expanded or collapsed. The entry bar 520 may be moved vertically to any location on the GUI by clicking and dragging it, or the entry bar 520 may quickly be moved to the top or bottom of the GUI by clicking the send to top button 504 or the send to bottom button 506, respectively. The entry area 235 may be expanded (allowing further data entry) by clicking on the expand button 502. The user may create a new cycle by clicking the New Cycle button 430.

The screen shot shown in FIG. 5, with the entry area 235 collapsed, may be used primarily to review records already stored in the database. For example, when a patient returns for a follow-up visit the cycle history area 510 provides a quick review of observations, categories, and actions, and more importantly provides the observation and action connections corresponding with each individual category. In another embodiment, the user can drag entries from the cycle history area into the cycle work area to create new entries. This would save the user from filling out a form. For example, a patient may have some of the same observations as on a previous visit, the patient may have the same category of care as on a previous visit, or the user may wish to repeat an action from a previous visit, e.g., refill a prescription.

FIGS. 6-8 show the SoapCycle software used in an automotive repair setting. The object of care is now an automobile, and the observations, categories of care, and actions are all related to the automobile. The observations 302 in FIGS. 6-8 include subjective and objective observations specific to the Volvo object of care 210. Observations include, among others, 'compression tests normal all cylinders,' 'maintenance free battery hydrometer window green,' and 'Fuel filter clean.' The categories column 204 may be used to enter and display the categories of care, such as preventative, normal, bad ignition switch, clogged fuel filter, etc. As with the veterinarian example of FIGS. 3-5, the categories are the central organizing axis of the record. The actions column 206 may be used to enter and display any actions taken or prescribed, such as new ignition switch, new fuel filter, and labor associated with any services performed.

FIG. 6 is a screen shot illustrating one embodiment of the SoapCycle software after entering data (observations, categories, and actions), but before adding connections between the three data types. As shown in FIG. 6, several observations 302, categories 304, and actions 306 related to the Volvo object of care 210 have been entered in to the current cycle. The data is entered into the SoapCycle interface in a manner similar to that described with respect to FIG. 3.

FIG. 7 is a screen shot illustrating one embodiment of the SoapCycle software after adding connections between the three data types. For example, FIG. 7 illustrates that observation 302d 'Ignition switch tests at 0 volts,' category 304d 'bad ignition switch,' and action 306d 'New ignition switch #1 and Labor replace ignition switch #1.25' have been connected by the connecting lines 440. The connections are made in a manner similar to that described with respect to FIG. 4.

FIG. 8 is a screen shot illustrating one embodiment of the SoapCycle software after completing an entry cycle. When each observation and action is connected to a category the current cycle is complete. For a detailed explanation of the process of completing an entry cycle, see FIG. 4.

As can be seen from the preceding examples, the Soap-Cycle software may be adapted to track an object of care in many different industries. The veterinarian (FIGS. 3-5) and automotive (FIGS. 6-8) examples illustrate the application of SoapCycle to two specific industries. These examples are not intended to limit the use of the SoapCycle software, but to illustrate the broad range of uses that are possible. It is contemplated that SoapCycle may be used in a similar manner to record observations, categories, and actions relating to an object of care in any other industry.

Figure 9:
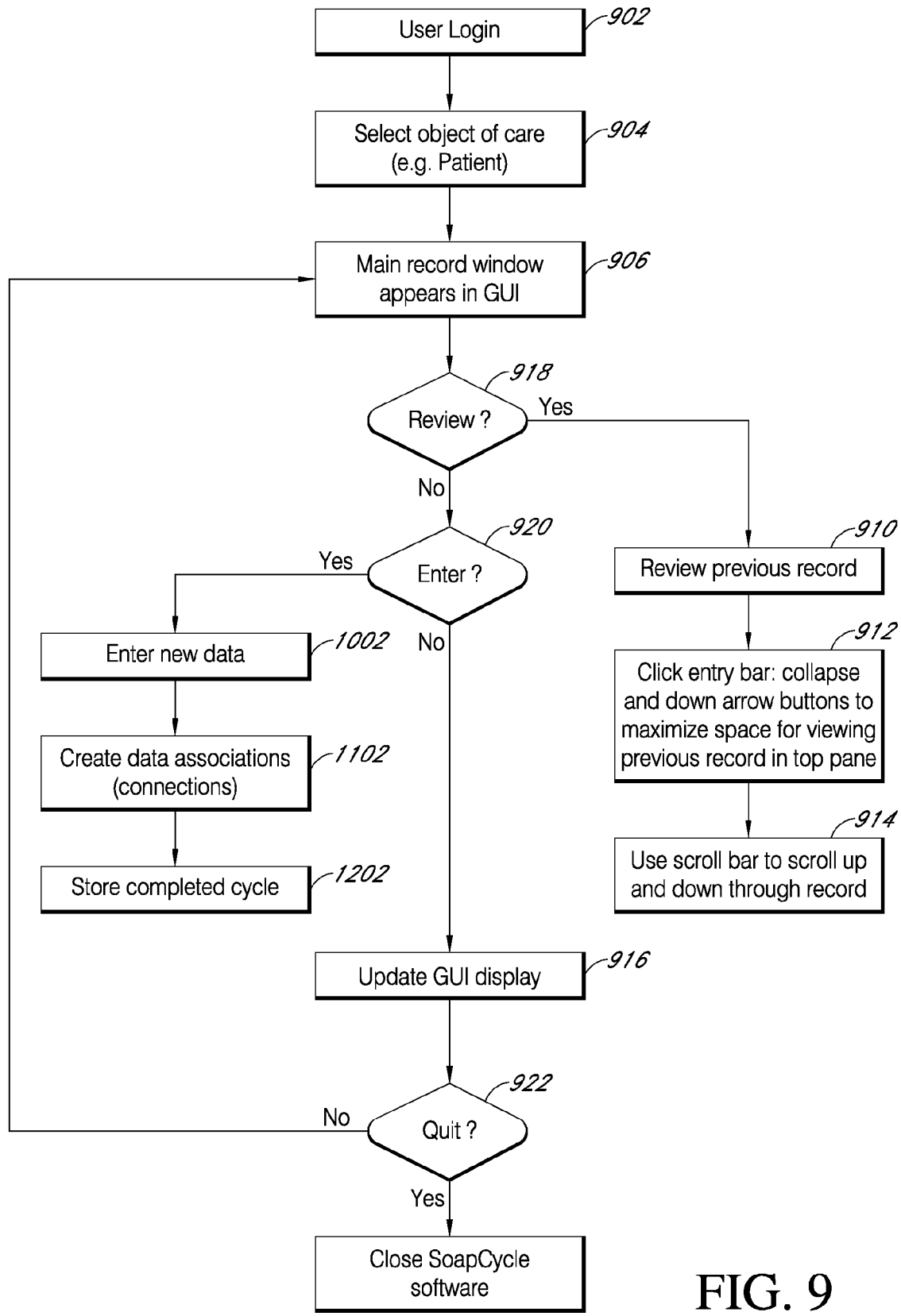
FIGS. 9-12 are flowcharts illustrating the method performed by a user in order to enter, organize, and view information stored by the SoapCycle software in one embodiment of the invention.

FIG. 9 is a flowchart illustrating one embodiment of the process performed by a SoapCycle user in operating the software. Certain blocks of FIG. 9 (blocks 1002, 1102, and 1202) have been expanded in FIGS. 10-12 in order to more fully illustrate certain aspects of the invention.

In block 902 the user logs in to the SoapCycle software. In one embodiment, each user has a unique login ID and password. In another embodiment, groups of users share a common login ID and password.

In block 904 the user selects the object of care that they want to enter/view data concerning. As stated above, an object of care may be a patient, client, customer, automobile, student, or any other object, whether living or inanimate.

In block 906 the SoapCycle main record window appears. The main record window displays information regarding the selected object of care 210 and allows entry of additional information. At this point the user may choose either to enter new data 1002 or review previous records 910.

In block 918, the user chooses whether or not to review a record. If the user decides to review a record, in block 910, the user reviews the previous record. In block 912 the user clicks the Enter bar and uses the collapse and down arrow buttons to maximize space for viewing the previous record in the top pane. In block 914 the user uses the scroll bar to scroll up and down through the record.

In block 920, the user chooses whether or not to enter new data. If the user decides to enter new data, the method proceeds through blocks 1002, 1102, and 1202, represented in FIGS. 10, 11, and 12, respectively. In brief, block 1002 allows the entry of new data, including categories of care, observations, and actions. In block 1102, the user creates associations between the entered data which are displayed as connection lines in the GUI. In block 1202, the newly entered data and associations are stored according to the storage configuration employed by the particular user.

After the user has completed a new data entry cycle (i.e. blocks 1002, 1102, and 1202) and/or a review record cycle (i.e. blocks 910, 912, and 914) the GUI display is updated and the user is presented with a series of decision blocks. More specifically, in block 916, the GUI display is updated to include any of the new data entered or changed during either an entry or review cycle. While the GUI update is illustrated at a specific location in the flowchart of FIG. 9, it is contemplated that the GUI is updates continuously as the user interacts with the SoapCycle software.

In block 922 the user decides whether to quit (i.e. exit) the SoapCycle software or continue viewing the main record window. If the user decides to quit, the SoapCycle software will be closed in block 924 and the user will need to Login (block 902) in order to again access the SoapCycle database. Alternatively, if the user does not elect to quit, the process returns to block 906 where the main record window is displayed. In one embodiment, the process, by default, flows from block 922 to step 906 without any input from the user until the user indicates a desire to quit. In other words, the user only exits the SoapCycle software by pressing a Quit or Exit button so that the process of FIG. 9 is repeated, without user input in block 922, until the Quit or Exit button is selected.

Figure 10:
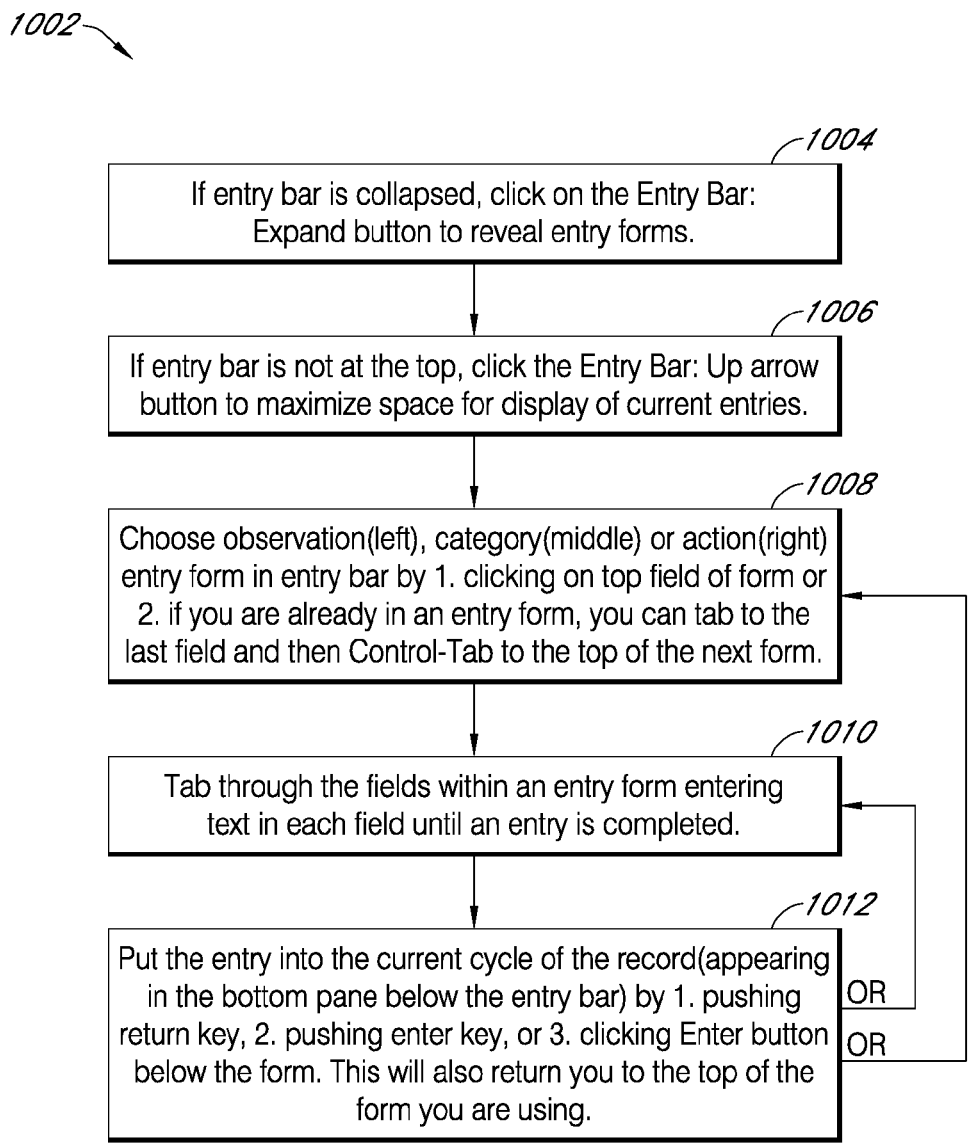

FIG. 10 is a flowchart illustrating one embodiment of the process of entering new data using the SoapCycle interface. FIG. 10 is an expanded version of block 1002 (FIG. 9), labeled Enter New Data.

In block 1004, if the entry bar is collapsed, the user clicks on the Entry Bar Expand button 502 (FIG. 5) to reveal entry forms.

In block 1006, if the entry bar is not at the top, the user clicks the Entry Bar Up arrow button to maximize space for display of current entries.

In block 1008, the user chooses either an observation (left), category (middle) or action (right) entry form. A specific entry form is selected by either clicking on the top field of form, or if the user is already in the entry form, Tabbing to the last field and then Control-Tabbing to the top of the next form.

In block 1010, the user tabs through the fields within an entry form, entering text in each field until an entry is completed.

In block 1012 the user puts the entry into the current cycle of the record (appearing in the bottom pane below the entry bar) by 1) pushing the return key, 2) pushing the enter key, or 3) clicking the enter button below the form. This will also return the user to the top field of the form he is using. At this point the user may either choose another observation, category or action entry form (block 1008) or continue to block 1102 to create data connections.

Figure 11:
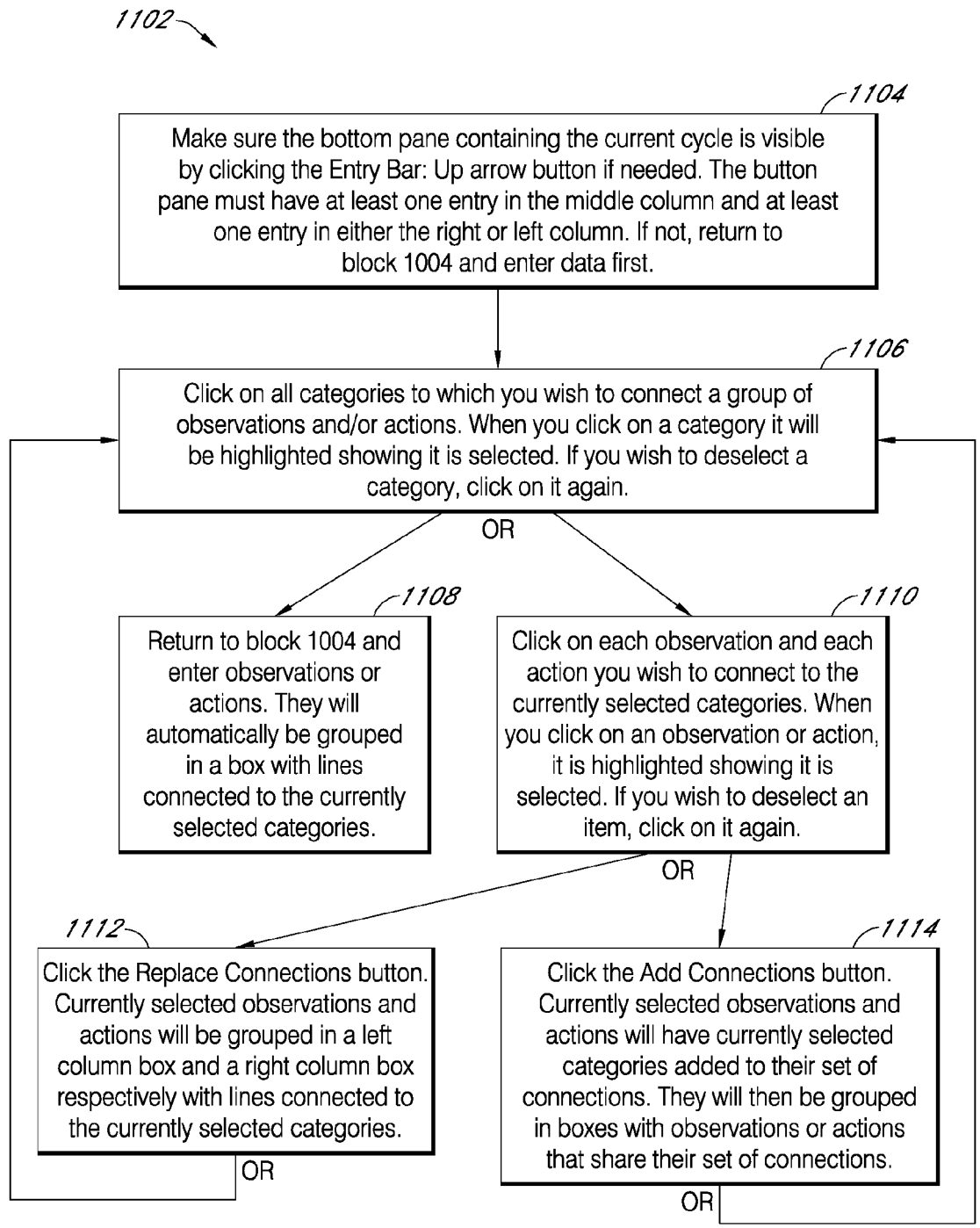

FIG. 11 is a flowchart illustrating one embodiment of the process of creating data connections using the SoapCycle interface. FIG. 11 is an expanded version of block 1102 (FIG. 9), labeled Create Data Connections. In block 1104, the user makes sure that the bottom pane containing the current cycle is visible by clicking the Entry Bar Up arrow button if needed. The bottom pane must have at least one entry in the middle column and at least one entry in either the right or left column. If not, the user returns to block 1002 and enters the data first.

In block 1106 the user clicks on all categories to which he wishes to connect a group of observations and/or actions. When he clicks on a category, it will be highlighted showing it is selected. If the user wishes to deselect a category, he clicks on it again. At this point the user has two options: (1) In block 1108 the user returns to block 1002 (FIG. 10) and enters additional observations or actions. The new observations or actions will automatically be grouped in a box with lines connected to the currently selected categories, or (2) adding additional connections by proceeding to block 1110.

In block 1110, the user clicks on each observation and each action he wishes to connect to the currently selected categories, highlighting the selected observations and actions. An item may be deselected by clicking on it again. At this point the user must choose either to replace existing connections (block 1112) or add new connection (block 1114)

In block 1112, the user clicks the Replace Connections button. Currently selected observations and actions will be grouped in a left column box and a right column box respectively with lines connected to the currently selected categories.

In block 1114, the user clicks the Add Connections button. Currently selected observations and actions will have currently selected categories added to their set of connections. They will then be grouped in boxes with observations or actions that share their set of connections.

After either block 1112 or 1114 is completed the user continues to block 1202 where the completed cycle is stored.

Figure 12:
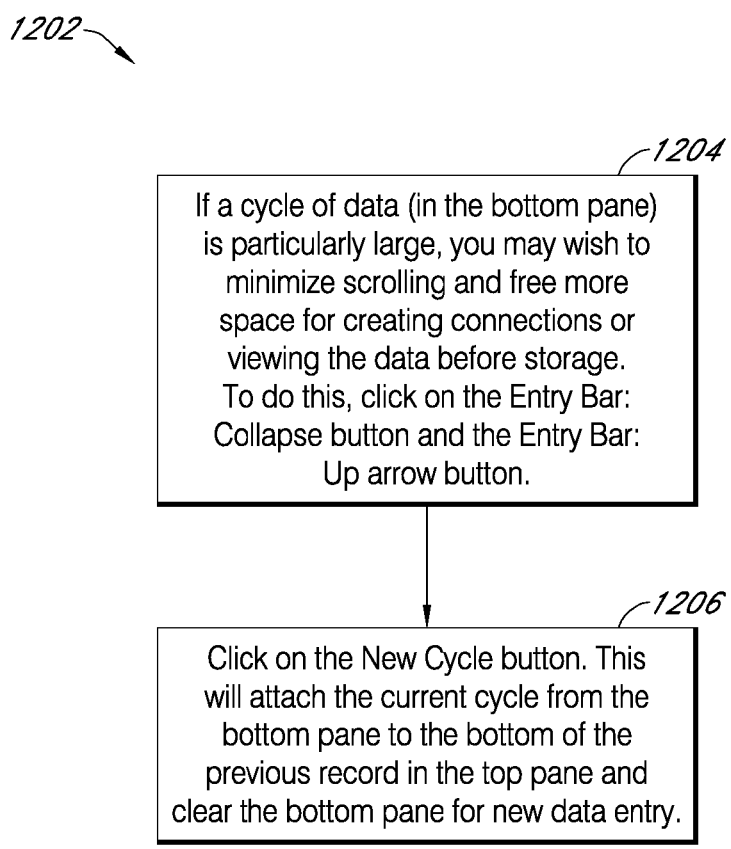

FIG. 12 is a flowchart illustrating one embodiment of the process of storing a completed cycle using the SoapCycle interface. FIG. 12 is an expanded version of block 1202 (FIG. 9), labeled Store Completed Cycle. In block 1204, if a cycle of data (in the bottom pane) is particularly large, the user may wish to minimize scrolling and free more space for creating connections or viewing the data before storage. To do this, the user clicks on the Entry Bar: Collapse button and the Entry Bar Up arrow button.

In block 1206, the user clicks on the New Cycle button. This will attach the current cycle from the bottom pane to the bottom of the previous record in the top pane and clear the bottom pane for new data entry. At this point, the user may choose to review previous records 910, enter new data 1002 or quit 1212.

Figure 13:
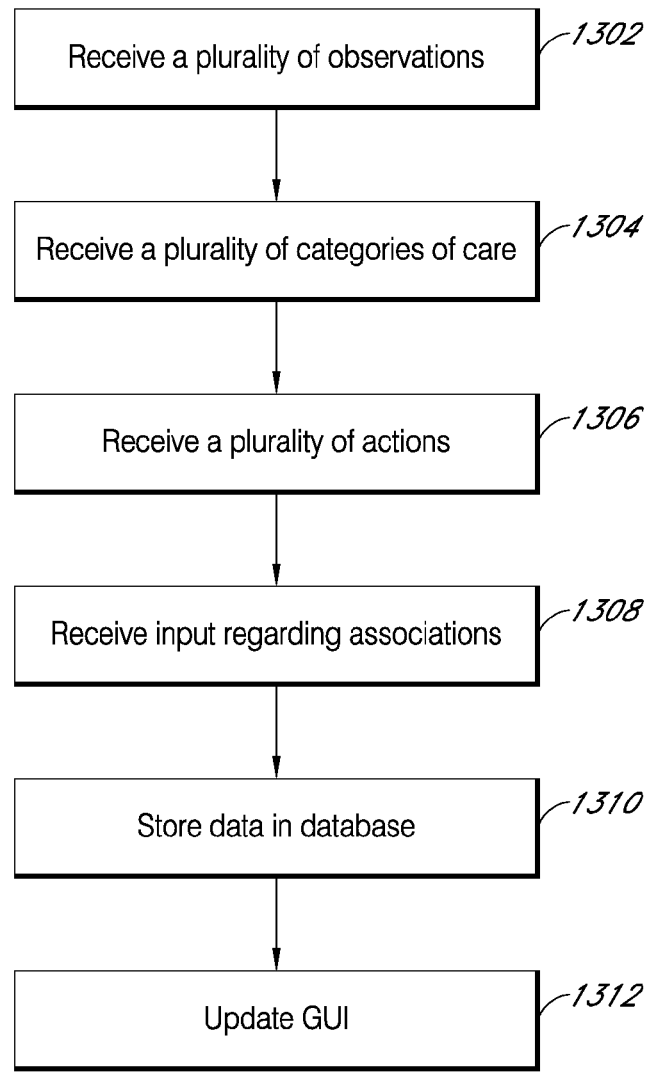
FIG. 13 is a flowchart illustrating one embodiment of the method performed by the SoapCycle software.

As indicated above, FIGS. 9-12 illustrate one embodiment of the process performed by a SoapCycle user in operating the software with respect to any object of care. Similarly, FIG. 13 is a flowchart illustrating one embodiment of the method performed by the SoapCycle software with respect to a particular object of care. As the process of FIG. 13 is performed, the software is periodically storing received information in memory, recording information in non-volatile memory, and/or storing information on a permanent storage medium according to any of a variety of known storage technique known in the programming art.

After a specific object of care has been selected (either by selecting an existing object of care or adding a new object of care), in block 1302, the software receives a plurality of observations regarding the object of care. In one embodiment the observations are entered using a keyboard connected to the computer running the SoapCycle software. However, it is contemplated that any of a variety of other known input device, such as a mouse, touchpad, or microphone, may be used to enter observations.

In block 1304, the software receives a plurality of categories of care. Again, the categories of care may be received by the software from an input device connected to the computer.

In block 1306, the software receives a plurality of actions meant for the object of care.

In block 1308, the software receives a plurality of associations between a particular category of care and one or more observations. In particular, after the user selects a specific category of care, the software receives the selection and may indicate the selection in the GUI by emphasizing, e.g., underlining or shading the selected category of care, for example. An association between the currently selected category of care and an observation is then stored by the software as the user selects a particular observation and clicks on the Add Connections button. If the particular category of care is still selected, or the user re-selects the same category of care, more observations may be associated with the particular category of care. In one embodiment, when more than one observation is associated with a particular category of care, the software displays the multiple observations in the GUI as a group. For example, the group 302A in FIG. 4 comprises five separate observations that were each associated with the category of care 304A. In another embodiment, the user may select a particular category of care and multiple observations before clicking on the Add connections button, thus resulting in substantially identical grouping in the GUI.

In block 1308, the software also receives a plurality of associations between a particular category of care and one or more actions. The selection and storage of associations between a category of care and actions is performed in a similar manner as discussed immediately above with respect to the observations. Likewise, the grouping of all actions associated with a particular category of care is automatically performed by the software.

In one embodiment, the software is capable of receiving data in blocks 1302, 1304, 1306, and 1308 in other sequences. For example, the software may receive, in temporal sequence, a category of care in block 1304, multiple observations in block 1302, an action in block 1306, another observation in block 1302, and then an association in block 1308.

In block 1310, the software stores received information in memory, records information in non-volatile memory, and/or writes information on a permanent storage medium. As mentioned above, block 1310 may operate to store information periodically throughout the process of FIG. 13. In one embodiment, the software may store information received from blocks 1302, 1304, 1306 and 1308 immediately after the information is received by the software. Occasionally, as indicated by the circumstances of the implementation, batches of the received data are accumulated in memory before they are stored in the main database (on a hard drive or network server, for example). The storage of batches of data may be advantageous when using a mobile data collection unit that is prone to disconnection from the main database or for reasons of efficiency and speed, such as a slow database connection. If problems are encountered storing a batch of data, the database may return a message indicating such and allowing the user to try again. In this embodiment, the database stores additional data relating to the status of synchronization between the two datastores.

In block 1312, the GUI is updated as soon as the software receives the data. In an advantageous embodiment, the software updates the GUI with information as soon as it is received. For example, after the software receives a new observation from the user controlled input device, the GUI is immediately updated to show the new observation.

Specific parts, shapes, materials, functions and modules have been set forth, herein. However, a skilled technologist will realize that there are many ways to fabricate the system of the present invention, and that there are many parts, components, modules or functions that may be substituted for those listed above. While the above detailed description has shown, described, and pointed out the fundamental novel features of the invention as applied to various embodiments, it will be understood that various omissions and substitutions and changes in the form and details of the components illustrated may be made by those skilled in the art, without departing from the spirit or essential characteristics of the invention.

What is claimed is:

1. A computing system for allowing data to be entered into a divider bar of a user interface configured to receive and display data regarding an object of care, the computing system comprising:

a storage device configured to store digital data, wherein the storage device stores a database comprising data including a plurality of object of care records, at least some of the object of care records comprising (a) at least one category of care associated with a respective object of care and (b) one or more observations or actions associated with respective of the at least one category of care;

a processor configured to execute software code in order to generate a window for display on a display device, the window including a work area configured to receive input from a user of the computing system indicating associations between respective categories of care and one or more observations and/or actions;

a history area configured to display each of the categories of care associated with a selected object of care and at least one observation or action associated with each of the categories of care;

a divider bar positioned between the work area and the history area, said divider bar having a collapsed state that separates the history area and the work area such that movement of the window on the display device moves each of the work area, the history area, and the divider bar concurrently as an integrated unit, and an expanded state comprising one or more text entry fields for receiving text data indicative of a category of care associated with the selected object of care, text data indicative of an observation associated with the category of care, and text data indicative of an action associated with the category of care, wherein the text data received in the one or more text entry fields is stored in the database and associated with the selected object of care, wherein the physical size of the divider bar in said expanded state is larger than the physical size of divider bar in said collapsed state such that the divider bar replaces at least some of the cycle history area or work area when in the expanded state, said divider bar comprising a selectable area having a first state and a second state, wherein when said selectable area is in a first state and said selectable area is selected, said divider bar expands to said expanded state and said selectable area enters said second state; when said selectable area is in said second state and said selectable area is selected, said divider bar collapses to said collapsed state and said selectable area enters said first state.

2. A method of providing access to a plurality of graphic objects on a computer display, comprising:

creating a generally rectangularly shaped graphic window comprising a plurality of graphic objects;

creating a generally rectangularly shaped divider graphic object ("divider") operable to separate said graphic window into two portions such that one or more of said plurality of graphic objects are disposed on either side of said divider, said divider comprising a collapsed state and an expanded state;

enabling a user to increase the physical area of said divider, when said divider is in said collapsed state, by changing the divider to said expanded state;

when the divider is in the expanded state, creating a category of care text entry field within the divider for receiving first textual data associated with an object of care, creating an observation text entry field within the divider for receiving second textual data associated with the first textual data, and creating an actions text entry filed within the divider for receiving third textual data associated with the first textual data;

storing in a data structure the first textual data, the second textual data, and the third textual data, wherein the second textual data and the third textual data are each associated with the first textual data in the data structure; and enabling a user to decrease the physical area of said divider when said divider is in said expanded state, by changing the divider to said collapsed state.

3. The method of claim 2, wherein said divider separates said graphic window horizontally, such that said graphic window comprises a top portion above said divider, and a bottom portion below said divider.

4. The method of claim 2, wherein said divider separates said graphic window vertically, such that said graphic window comprises a left portion to the left of said divider, and a right portion to the right of said divider.

5. A computing readable medium for storing software instructions for execution by a processor of a computing device, the software instruction causing the computing device to:

store a database comprising data regarding a plurality of object of care records, at least some of the object of care records comprising (a) at least one category of care associated with a respective object of care and (b) one or more observations or actions associated with respective of the at least one category of care;

generate a window for display on a display device, the window including a work area configured to receive input from a user of the computing system indicating associations between respective categories of care and one or more observations or actions;

a history area configured to display each of the categories of care associated with a selected object of care and at least one observation or action associated with each of the categories of care; and a divider bar positioned between the work area and the history area, said divider bar having a collapsed state wherein the divider bar separates the history area and the work area such that movement of the window moves each of the work area, the history area, and the divider bar, and an expanded state comprising one or more text entry fields for receiving text data indicative of a category of care associated with the selected object of care, and one or more of text data indicative of an observation associated with the category of care and text data indicative of an action associated with the category of care, wherein the text data received in the one or more text entry fields is stored in the database and associated with the selected object of care, wherein the physical size of the divider bar in said expanded state is larger than the physical size of divider bar in said collapsed state such that the divider bar replaces at least some of the cycle history area or work area when in the expanded state.

\* \* \* \* \*